US009210934B2

(12) United States Patent
Ryan et al.

(10) Patent No.: US 9,210,934 B2
(45) Date of Patent: Dec. 15, 2015

(54) SURFACE COATING

(71) Applicant: Dublin Institute of Technology, Dublin (IE)

(72) Inventors: Darragh Ryan, Dublin (IE); Suresh Pillai, Sligo (IE); Joanna Carroll, Dublin (IE)

(73) Assignee: Dublin Institute of Technology (IE)

( * ) Notice: Subject to any disclaimer, the term of this patent is extended or adjusted under 35 U.S.C. 154(b) by 0 days.

(21) Appl. No.: 14/569,160

(22) Filed: Dec. 12, 2014

(65) Prior Publication Data

US 2015/0164081 A1    Jun. 18, 2015

(30) Foreign Application Priority Data

Dec. 18, 2013 (GB) .................................. 1322436.5

(51) Int. Cl.

| A01N 59/00 | (2006.01) |
|---|---|
| A01N 59/20 | (2006.01) |
| C01G 23/053 | (2006.01) |
| A01N 55/02 | (2006.01) |
| A01N 37/02 | (2006.01) |
| B05D 1/02 | (2006.01) |
| B05D 1/18 | (2006.01) |

(52) U.S. Cl.
CPC ................ *A01N 55/02* (2013.01); *A01N 37/02* (2013.01); *A01N 59/00* (2013.01); *A01N 59/20* (2013.01); *B05D 1/02* (2013.01); *B05D 1/18* (2013.01); *C01G 23/053* (2013.01)

(58) Field of Classification Search
CPC ....... A01N 37/02; A01N 55/02; A01N 59/00; A01N 59/16; A01N 59/20; C01G 23/00; C01G 23/053
USPC ...................................................... 106/15.05
See application file for complete search history.

(56) References Cited

U.S. PATENT DOCUMENTS

| 6,074,981 | A | 6/2000 | Tada et al. |
|---|---|---|---|
| 6,194,346 | B1 * | 2/2001 | Tada et al. ..................... 502/224 |
| 6,337,370 | B1 * | 1/2002 | Bae et al. ......................... 525/61 |
| 8,551,909 | B2 | 10/2013 | Etacheri et al. |
| 2002/0135001 | A1 * | 9/2002 | Gaucher ....................... 257/295 |
| 2003/0235653 | A1 | 12/2003 | Yu |
| 2010/0316561 | A1 * | 12/2010 | Ciccarella et al. ............ 423/610 |
| 2011/0028311 | A1 * | 2/2011 | Etacheri et al. ............... 502/200 |
| 2013/0122074 | A1 | 5/2013 | Kerrod et al. |

FOREIGN PATENT DOCUMENTS

| CN | 101422165 A | 5/2009 |  |
|---|---|---|---|
| CN | 102989456 A | 3/2013 |  |
| FR | 2971519 A1 * | 8/2012 | ............. C23C 16/40 |
| GB | 2039865 A | 8/1980 |  |
| WO | 2008005055 A2 | 1/2008 |  |
| WO | 2008005055 A3 | 1/2008 |  |
| WO | 2009113045 A2 | 9/2009 |  |
| WO | 2010088513 A2 | 8/2010 |  |
| WO | 2012007534 A2 | 1/2012 |  |

OTHER PUBLICATIONS

Application No. GB 1322436.5 Combined Search and Examination Report under Sections 17 and 18(3), dated Jun. 18, 2014.
Application No. GB 1322436.5 Patent Act 1977: Search Report under Section 17(6), dated Dec. 1, 2014.
International Search Report, PCT/EP2014/077561, mailed Feb. 2, 2015.

* cited by examiner

*Primary Examiner* — Anthony J Green
(74) *Attorney, Agent, or Firm* — One3 IP Management, P.C.; Jeromye V. Sartain

(57) ABSTRACT

A process for the preparation of an antimicrobial coating solution is described. The process comprises the steps of: (i) mixing a chelating agent with titanium alkoxide and fluoroacetic acid; and (ii) adding an aqueous solution to the mixture from step (i). The antimicrobial coating described is visible light activated. The coating is applied to surfaces and then heat treated to form a transparent layer on the surface. This is particularly advantageous where the surface is glass.

30 Claims, 2 Drawing Sheets

US 9,210,934 B2

SURFACE COATING

RELATED APPLICATIONS

This application claims priority and is entitled to the filing date of United Kingdom Patent Application GB1322436.5 filed on Dec. 18, 2013, entitled "A Surface Coating." The contents of the aforementioned application are incorporated by reference herein.

FIELD

The present application relates to coatings for surfaces and more particularly to anti-microbial coatings.

BACKGROUND OF THE INVENTION

An antimicrobial surface is one that presents an antimicrobial agent that inhibits or reduces the ability of microorganisms to grow. Antimicrobial agents are agents that kill microorganisms or inhibit their growth. Antimicrobial agents can be classified by the microorganisms that they act against. For example, antibacterials are used against bacteria, anti-fungals are used against fungi and anti-virals are used against viruses.

Such surfaces are desirable to prevent the spread of infection and so are desirable in healthcare settings such as hospitals, hospices, retirement homes and clinics, for example. However they are equally desirable in other settings including the home, community, transport, office environment or other public and private areas.

Whilst a material may or may not be inherently antimicrobial, the present application is directed generally to surfaces which do not possess inherent or sufficient antimicrobial properties and require a surface treatment or coating to become antimicrobial.

One area, where research has been focussed is the antimicrobial properties of copper and its alloys (brasses, bronzes, cupronickel, copper-nickel-zinc, and others). These antimicrobial materials have intrinsic properties which can destroy a wide range of microorganisms. As a result, copper and copper alloy surfaces are an effective means for preventing the growth of bacteria. Silver and zinc are also known for use in the field of antimicrobial agents.

An alternative approach is that of photocatalytically active pigments such as titanium dioxide ($TiO_2$) or zinc oxide ($ZnO$) which have been used on glass, ceramic, and steel substrates for self-cleaning and antimicrobial purposes. The term "photocatalytically active pigment" means that the pigment uses the power of visible and ultraviolet light to generate oxidising agents on treated surfaces that destroy microorganisms such as bacteria, fungi and viruses on the surfaces.

For example, $TiO_2$ reacts with light of appropriate wavelength resulting in the activation of $TiO_2$, and creates a number of reactive oxygen species (ROS) such as hydroxyl radicals and superoxide anions after reacting with atmospheric oxygen and water. This can be explained by the following equations:

$$TiO_2 + \text{Light}\ (hv) \rightarrow \text{Photogenerated hole}\ (h^+_{VB}) + \text{Electron}\ (e^-_{CB}) \quad (1)$$

$$\text{Water}\ (H_2O) + h^+_{VB} \rightarrow \cdot OH + H^+ \quad (2)$$

$$\text{Oxygen}\ (O_2) + e^-_{CB} \rightarrow O_2^{-} \quad (3)$$

The hydroxyl radical as ROS is mainly responsible for the anti-microbial action, although other ROS such as singlet oxygen, hydrogen peroxide and the superoxide radical have also been reported to be involved in the process.

Titania has been used as an antimicrobial, self-cleaning, or depolluting coating on tiles, paving slabs, deodorizers, self-cleaning windows, and many more. Such an approach is described in WO2010064225-A1, in which a process for synthesising a visible light active high temperature stable anatase phase undoped titanium dioxide photocatalyst is provided comprising the step of reacting hydrated titanium dioxide with hydrogen peroxide in an aqueous solution to form a sol.

However, the processing described in WO2010064225-A1 is time consuming as it involves multiple processing steps. The sol is also unstable and is solvent based.

Furthermore, the coating in WO2010064225-A1 is more suitable for use with substrates having a high temperature stability such as ceramic tiles or roof tiles for example, which are processed above 1000° C. Glass will soften and will lose its morphological properties at a temperature typically just over 700° C. depending on the type of glass.

U.S. Pat. No. 8,551,909B describes a method of making a photocatalyst comprising a visible light activatable mesoporous titanium dioxide. The process mixes titanium isopropoxide with boiling water and the resulting solution with precipitated hydrated titanium oxide was then microwaved, filtered and dried to produce a white powder. This powder may be used as an additive for a non-transparent antimicrobial coating.

In addition, many antimicrobial coatings that are currently available require UV light for activation. UV light may not be readily available in many indoor environments where there is a need for antimicrobial coatings, for example in hospitals, clinics, offices, public transport or other community areas.

Despite developments in the field of antimicrobial coatings, there remains a need for improved antimicrobial coatings and processes for the preparation and deposition of such coatings.

SUMMARY

Accordingly, in one aspect, the present teaching provides a process for the preparation of an antimicrobial coating solution, the process comprising the steps of:
(i) mixing a chelating agent with titanium alkoxide and fluoroacetic acid; and
(ii) adding an aqueous solution to the mixture from step (i).

It is to be understood that in the preferred embodiment, the aqueous solution comprises solely water as the solvent. However, in an alternative embodiment, the aqueous solution can also comprise organic solvents such as alcohols including, but not limited to, ethanol, methanol or isopropanol, in an amount up to 80 water:20 organic solvent. However, this inclusion of an organic solvent would increase the cost and the 'carbon foot print' would be higher than in the embodiments in which the aqueous solution relies entirely on water as the solvent.

An advantage of the process according to the present teaching is that it allows for a thin homogeneous coating to be applied to a substrate (in this context, the term "thin" means approx 80 nm to 200 nm thickness for a single layer) and still provide for effective antimicrobial action, the end product being transparent to the user.

The addition of an aqueous solution is counter intuitive because normally the addition of water would cause the titanium to precipitate out. However it has been found that by using a high ratio of the aqueous solution to the other components that precipitation is avoided. The term, "high ratio" means above 50 moles times (e.g for every 1 mole of titania precursor 50 or more mole times aqueous solution is required). Ideally, between 90 to 200 mole times is used to ensure full dissolution). (Any solvent ratio lower than 50 mole times would not achieve the advantageous results of the present invention).

In this specification, weight % (wt %) is to be construed as meaning weight % relative to the weight of the total composition.

The chelating agent may be a carboxylic acid.

The carboxylic acid may be selected from the group consisting of formic acid, propionic acid, butanoic acid and acetic acid.

Preferably, the carboxylic acid is acetic acid. The preferred form of acetic acid is glacial acetic acid. Where the acetic acid is selected as the chelating agent, the preferred form is glacial acetic acid to prevent reaction between water and the titanium alkoxide prior to the step of adding the aqueous solution.

The amount of glacial acetic acid used may be in the range 1 to 40 wt %; preferably in the range 1 to 20%; and most preferably, in the range 2 to 10 wt %; and with the range 12 to 18 wt % being optional.

The titanium alkoxide may be selected from the group consisting of titanium isopropoxide, titanium ethoxide, titanium methoxide and titanium butoxide. The preferred titanium alkoxide is titanium isopropoxide as its performance has been clearly demonstrated to provide an effective coating solution.

The amount of titanium isopropoxide used may be in the range 4 to 15 wt %, preferably 6 to 12 wt %.

The fluoroacetic acid may be one of monofluoroacetic acid, difluoroacetic acid or trifluoroacetic acid. Preferably, the fluoroacetic acid is trifluoroacetic acid. Where monofluoroacetic acid or difluoroacetic acid is employed, the amount used may be varied relative to the amount of trifluoroacetic acid so that the amount of fluorine present remains consistent.

The amount of trifluoroacetic acid used may be in the range 0.1 to 20 wt %, preferably in the range 0.1 to 10 wt % and most preferably 2 to 8 wt %.

The process according to the present teaching may comprise the step of adding a metal precursor. A metal precursor may be added to improve or alter the antimicrobial action.

The metal precursor may be one of copper, silver or zinc.

The metal precursor may be a sulphate or nitrate of the metal. Copper and Silver act as electron donors directly to the conduction band of $TiO_2$. Zinc may form a heterojunction to reduce electron hole recombination.

Where the metal comprises copper, the copper precursor may be selected from, but not limited to, the group consisting of copper nitrate, copper nitrate pentahemihydrate, copper chloride, copper acetate and copper sulphate.

In a preferred aspect of the present teaching, the metal precursor is copper (II) nitrate pentahemihydrate.

The amount of copper (II) nitrate pentahemihydrate used may be in the range 0.03 to 3 wt %; preferably in the range 0.3 to 3 wt %; and most preferably, in the range of 0.1 to 2.8 wt %; ideally, in the range of 0.5 to 2.8 wt %.

The copper (II) nitrate pentahemihydrate may be dissolved within the aqueous solution prior to the step of adding the aqueous solution to the mixture from step (i).

The amount of water used may be in the range 30 to 99.5 wt %, preferably 40 to 99 wt %; and most preferably, 50 to 95 wt %. (Wt % water compared to the wt of the total composition).

The process may be carried out at a temperature between 15 and 25° C.

In one aspect, the present teaching provides a process for making an antimicrobial powder, the process comprising the initial step of preparing a solution in accordance with the process described herein and then annealing the solution at a temperature between 350° C. and 1350° C.

In a further aspect, a method of preparing an antimicrobial coating is provided, the method comprising the step of mixing an antimicrobial powder as prepared by the process described herein, with a coating composition.

Preferably, the coating composition comprises an aqueous solution and the method comprises the step of fluorinating the solution with a fluorinating agent. The fluorinating agent may be one of trifluoroacetic acid and sodium fluoride.

A visible light activated antimicrobial coating composition is obtained by the method described herein. The coating described herein can be used under indoor lighting conditions. The antimicrobial coating composition exhibits antimicrobial activity under visible light and in reduced light.

The antimicrobial compositions described herein are stable at high temperatures. Suitably, the antimicrobial coatings composition described herein is stable at temperatures up to at 1350° C.

A method for coating a substrate is provided, the method comprising the steps of
  (i) depositing an antimicrobial coating solution prepared according to the process described herein or an antimicrobial coating composition described herein, on a substrate;
  (ii) drying said coating; and
  (iii) exposing the coated substrate to a temperature above 300° C. for a period of time in the range 20 minutes to 3 hours.

The coated substrate may be exposed to a temperature in the range 300° C. to 1350° C. Where the substrate is glass or comparable composite material, the temperature is preferably in the range of 350° C. to 600° C., most preferably 450° C. to 550° C. In a preferred embodiment, the coated substrate is exposed to a temperature of 500° C.

In the case where the substrate is a ceramic material, the third step (iii) may be a firing process. The temperature may be between 500-700° C. for a second firing step or the temperature may be between 1100-1350° C. for a firing process having a single firing.

Suitably, the composition according to the present teaching can be applied in liquid form to a substrate to provide a coating.

The liquid coating may be deposited by any suitable method. Suitable methods may include but are not limited to spraying, dipping, roller, brush, electrostatic and spin-coating.

The present teaching provides an antimicrobial coating composition comprising a hydrolysed fluorine- and copper-doped titanyl acetate transparent sol.

The present application further provides an antimicrobial coating comprising a transparent fluorine- and copper doped titania coating.

Suitably, the present application provides an antimicrobial coating composition comprising fluorine-doped titanyl acetate. Advantageously, this may be in the form of a gel which may be packaged and shipped to locations where the coating composition is be applied. The advantage being that the coating composition may be manufactured and packaged for shipping in relatively small amounts reducing packaging and shipping costs. A further advantage is that the shelf life is effectively lengthened by at least several months. At the location of the coating process, water may be added as required. At the same time, a metal precursor such as for example copper, may be added. Once the water is added the fluorine-doped titanyl acetate is hydrolysed.

The present teaching further provides a kit comprising (i) an antimicrobial coating composition comprising fluorine-doped titanyl acetate and (ii) copper (II) nitrate pentahemihydrate.

In a further aspect, the present teaching provides a coated substrate comprising an antimicrobial coating prepared by the process described herein or an antimicrobial coating composition described herein.

The substrate may be selected from the group consisting of glass and related composite materials, ceramics, plastic, cement and clay. Where the substrate is glass, the glass may be, for example, a chemically strengthened glass or tempered glass. In specific applications, the substrate may be a clay brick, ceramic tile or element of sanitary ware.

BRIEF DESCRIPTION OF THE DRAWINGS

The present application will now be described with reference to the accompanying drawings in which.

DETAILED DESCRIPTION

Figure 1:
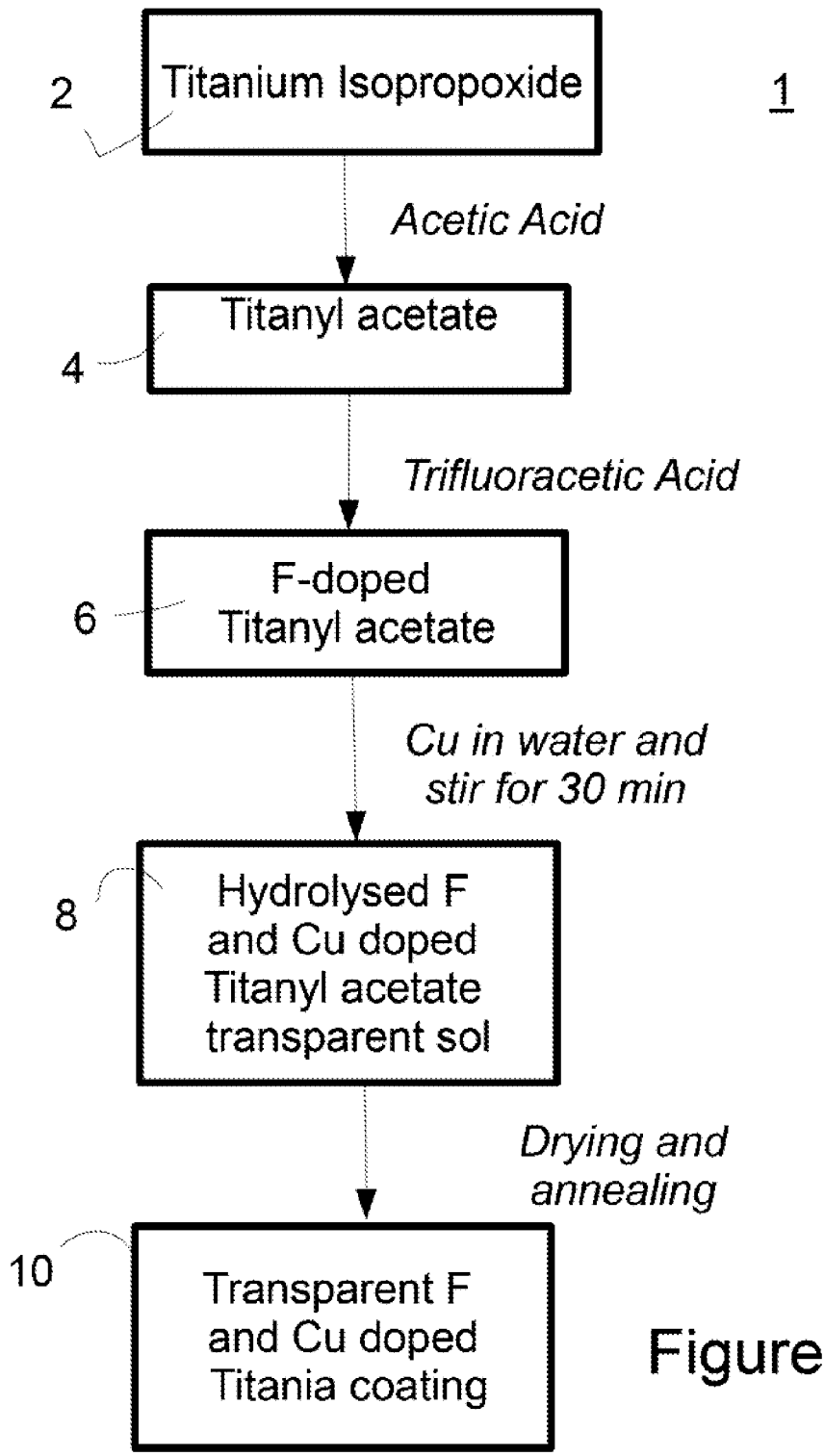
FIG. 1 is a schematic showing the intermediate stages in a process for forming a coating according to one aspect of the present invention.

The present application provides an industrially viable water-based environmentally benign, processing technology for the production of antimicrobial coating solutions.

The anti-microbial coating solution described herein is eco-friendly which is highly desirable. The solution used is water based. An advantage of the water based sol according to the present teaching is that it is easy to spray and is environmentally benign as it contains little or no volatile organic compounds. A further advantage of the water based composition is that it can be readily applied as a topcoat to a surface.

The composition described herein provides visible light induced antimicrobial action. It can be considered to be an effective antimicrobial agent against a range of pathogens including gram positive bacteria, gram negative bacteria, viruses and fungi, for example.

The process described herein enables the production of an immobilised antimicrobial coating on a substrate. A further advantage is that the coating is effectively transparent on glass. The sol described herein may be applied to surfaces using conventional spray, automated machine spraying, application by brush or dipping processes. Once applied, the sol may be dried and then heated to fuse with the glass, ceramic or other substrate material of the underlying surface to form a coating.

The coating provides a photocatalytic antimicrobial coating.

The term "photocatalytically active antimicrobial coating" means that the coating uses the power of light to generate oxidising agents on a surface that destroys microorganisms such as bacteria, fungi and viruses on the surface. The light required is natural room light (including fluorescent, LED and incandescent sources) or sunlight.

The term "antimicrobial coating" as used herein means a coating that kills or inhibits the growth of microorganisms including bacteria, fungi and viruses, for example.

The selection of the various constituents of the sol according to the present teaching is important to ensure that the sol is effective and usable in an industrial context.

The antimicrobial coating according to the present teaching comprises a number of different components including a precursor for forming a titanium dioxide coating when applied to a surface. The precursor is, titanium alkoxide suitably, titanium isopropoxide. An additive can be included in the formulation to assist the resulting titanium dioxide antibacterial functionality in the presence of visible light. To stabilise the sol and ensure an adequate shelf life, an optimised volume of glacial acetic acid may be included.

Where dopants are added to the formulation, e.g. Cu, the coating also demonstrates antimicrobial activity in conditions of reduced light or darkness. For example, a copper precursor can be added to improve the antimicrobial activity of the coating composition. It is suggested that the copper improves photocatalysis by supplying electrons to the $TiO_2$ and also by the action of copper ions. In the dark, the anti-bacterial action is believed to arise principally from the action of copper ions. Examples of copper precursors include Copper nitrate pentahemihydrate, Copper acetate and Copper sulphate. Copper nitrate pentahemihydrate is advantageous in that it provided the best results for stability and effectiveness and was best for solubility.

The invention will be described in more detail below with reference to the following example in which an exemplary formulation and method of preparation of same is described. In the context of the description below pure VLA refers to a formulation which does not include a copper precursor and doped VLA refers to a formulation including a copper precursor.

The exemplary formulation for producing doped VLA comprises titanium isopropoxide, trifluoroacetic acid, glacial acetic acid, copper nitrate pentahemihydrate and water.

EXAMPLE

Materials

Titanium isopropoxide (TIPP) ($C_{12}H_{28}O_4Ti$) (Grade 97%; supplied by Sigma Aldrich under CAS Number: 546-68-9 (Cat. Number of supplier 205273-2L); Trifluoroacetic acid (TFA) ($C_2HF_3O_2$) (Grade 99%, supplied by Sigma Aldrich as CAS Number: 76-05-1 (Cat. Number of supplier T6508-1 L); Glacial acetic acid (ACS≥99.7%; supplied by Sigma Aldrich under CAS Number: 64-19-7, Cat. Number of supplier 320099-2.5L); Deionised water;

and, where employed, Copper (II) nitrate pentahemihydrate (Grade Puriss ACS; CAS Number: 10031-43-3 available from Riede-de Haën, of Germany as Cat. Number of supplier 31288).

The following sets out examples of ranges of each component that may be used for preparing a pure VLA solution and a doped VLA solution.

Weight Percentages

Example of Pure VLA

Deionised water=(Range 40 to 99%, preferably 50 to 95%)

Titanium isopropoxide=(Range 4 to 15%)

Trifluroacetic acid=(Range 1 to 10%)

Glacial acetic acid=(Range 10-20%)

Example of Doped VLA

Deionised water=(Range 50 to 95%)

Titanium isopropoxide=(Range 4 to 15%)

Trifluroacetic acid=(Range 0.1 to 10%)

Glacial acetic acid=(Range 10-40%)

Copper (II) nitrate pentahemihydrate=(Range 0.3 to 3%)

The following table sets out the materials and amounts of each used for the formulation in this example for doped VLA.

TABLE 1

| Name | Grade | Amount | % wt |
|---|---|---|---|
| Titanium isopropoxide (TIPP)($C_{12}H_{28}O_4Ti$) | 97% | 12.5 mL | 6.5% |
| Trifluoroacetic acid (TFA) ($C_2HF_3O_2$) | 99% | 4 mL | 2.08% |
| Glacial acetic acid | ACS ≥99.7% | 24 mL | 12.50% |
| Deionised water | N/A | 150 mL | 78.16% |
| Copper (II) nitrate pentahemihydrate | Puriss ACS | 1.393 g | 0.72% |

Method 1 Pure VLA

All glassware required for the process (for example, beakers and measuring cylinder) was washed and dried.

In order to prepare the formulation, glacial acetic acid (24 mL glacial acetic acid) was added to a glass beaker while continuously stirring at room temperature. Next, titanium isopropoxide (12.5 mL) was added slowly in a dropwise manner, and the mixture allowed to continue stirring for a period of 30 minutes. Then trifluoroacetic acid (4 mL) was added dropwise and the solution was left to stir for 10 minutes. The final step is the addition of water (150 mL), which was added in a dropwise manner and stirred for a further 30 minutes to one hour.

Method 2: Doped VLA Coating

All glassware required for the process (for example, beakers and measuring cylinder) was washed and dried.

In order to prepare the formulation, glacial acetic acid (24 mL glacial acetic acid) was added to a glass beaker while continuously stirring at room temperature. Next, titanium isopropoxide (12.5 mL) was added slowly in a dropwise manner, and the mixture allowed to continue stirring for a period of 30 minutes. Then trifluoroacetic acid (4 mL) was added dropwise and the solution was left to stir for 10 minutes.

In the meantime the copper precursor, Copper (II) nitrate pentahemihydrate (1.393 g) was added to water (150 ml), completely dissolved and then added slowly to the previously prepared solution. At this stage a transparent, blue solution was obtained which was left to mix for another 30 minutes. In order to remove any remaining agglomerates, the obtained formulation was filtered using 0.22 μm syringe filter and stored in the fridge prior to coating on a substrate.

It will be appreciated by the skilled person that the method according to one aspect of the present teaching has been discussed with reference to experiments conducted in a laboratory but that the process described may readily be scaled for industrial production. For production of the coating according to the present teaching on an industrial scale, the same percentages of components may be used to make up the formulation to 100 L or more depending on the equipment available. The process is suitably carried out in a substantially dry environment, that is, one where there is little or no excess moisture. The process is suitably carried out at room temperature and with suitable agitation. One of the most important parts of the process is to ensure that the precipitate of titanyl acetate agglomerate is fully dissolved. This step may take more than 30 minutes to achieve and may require vigorous agitation/stirring.

Figure 2:
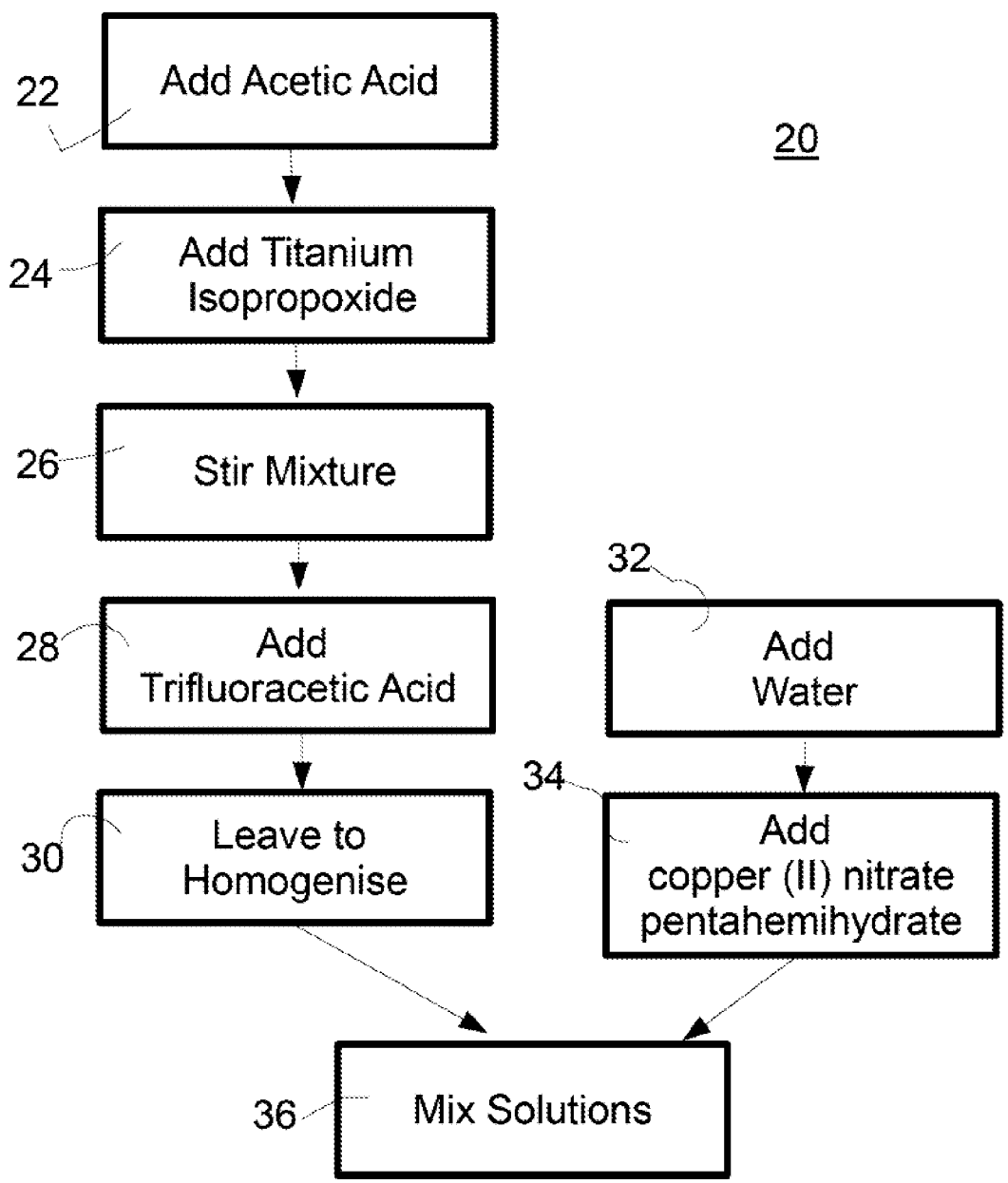
FIG. 2 is a flow chart providing detail on the steps of the process set out in FIG. 1.

The process 1, 20 described herein which is illustrated with reference to FIGS. 1 and 2 suitably comprises simple and industrially viable processing steps. With reference to the example above, the method according to one aspect of the present teaching commences with an amount of acetic acid at step 22 placed in a mixing container. The mixing container may be any suitable container. For example, in a laboratory setting a clean, dry glass beaker may be employed. The acetic acid is preferably glacial acetic acid. The use of normal water-based acetic acid is not desirable as the formulation may precipitate out. The amount of glacial acetic acid used in the laboratory setup is notionally 24 mL, but may be in the range of 20 to 40 mL (10-20%).

In a following step titanium isopropoxide 2 was added slowly at step 24. The amount of titanium isopropoxide used is suitably in the range 10 to 20 mL. The amount used in the example above was 12.5 mL. This mixture was stirred at step 26 for a suitable time to ensure adequate mixing. The mixture may be stirred for a period of time from 5 minutes to 120 minutes. In the laboratory setting, 30 minutes was sufficient to ensure adequate mixing. This resulted in titanyl acetate 4.

After this step, trifluoroacetic acid was added slowly at step 28. The amount of trifluoroacetic acid (TFA) ($C_2HF_3O_2$) used in the example was 4 mL. Trifluoroacetic acid may be used in an amount in the range 2 mL-20 mL (1 to 10%). This resulted in F-doped titanyl acetate 6.

Trifluoroacetic acid is used as a compatible F-dopant precursor in the system. F is added to reduce the band gap of titania to induce visible light activity. TiO2 has a band gap of 3.2 eV and shows a relatively high anti-bacterial activity under ultraviolet (UV) light (wavelength<390 nm), but introduction of UV light is not practical in hospitals or community areas. If the band gap of titania is lowered, titania can be activated by using visible light. Therefore, the introduction of fluorine as a dopant reduces the band gap of titania. This enables the formulation according to the present teaching to be visible light activated as the photocatalyst will be will activated in visible light.

Following the addition of trifluoroacetic acid, the resulting solution was left to homogenize 30. In the laboratory setting, 10 minutes was sufficient for this purpose.

As discussed above, in a separate step, the copper component, suitably copper (II) nitrate pentahemihydrate was added 34 to an amount of water 32. The amount of copper (II) nitrate pentahemihydrate used may be in the range 0.65 to 4.5 g (0.3 to 3%). The amount of deionised water used in the process described herein may be in the range 75-1000 mL (60 to 90%). In the example above, the copper component is suitably of the amount of 1.393 g added to 150 ml of water (preferably, deionised).

The water and copper components were mixed to ensure the copper component was completely dissolved. The mix was then added slowly at step 36 to the previously prepared solution which had been left to homogenise. At this stage, a transparent, blue solution was obtained which was left to mix for another 30 minutes. This results in the formation of a hydrolysed F and Cu doped titanyl acetate transparent sol 8.

To improve the effectiveness of the sol, a filtering step was performed to remove any remaining agglomerates. In the laboratory setting, the formulation was filtered using 0.22 μm syringe filter.

Prior to depositing a coating according to the present teaching on a substrate, the substrate should be cleaned to remove any impurities. For example, the substrate may be cleaned using soap and hot water to remove any dirt.

Substrates may be pre-treated prior to coating. For example, the substrate may undergo cleaning by mechanical means or with surfactants, or alcohols or organic or inorganic cleaners or plasma etching etc. Examples can include piranha etch (a mixture of sulfuric acid ($H_2SO_4$) and hydrogen peroxide ($H_2O_2$), used to clean organic residues off glass substrates).

To treat a surface or substrate, the sol prepared in accordance with the process of the present teaching may be applied to a surface using any suitable deposition technique which may include spraying, dip-coating, roller, brush or electrostatic spray for example. Exemplary spray techniques include HVLP (High velocity low pressure) and conventional spray using compressed air.

Once the sol is applied to a surface, it is left to dry. Whilst the drying may be accelerated using conventional techniques (such as oven, IR heaters, convection heaters, for example.), the surface is generally dry within a couple of hours. For example, the coated surface may be dry within a period of 2 to 24 hours, preferably within 12 to 18 hours.

Whilst the coating may be effective in this dry state, its adherence to the surface is limited and antimicrobial performance may be improved using a further step. This further step exposes the coating and surface to an elevated temperature for a period of time to allow the coating to fuse with the surface layer of the surface. Anatase phase of the $TiO_2$ is formed during this stage of the process. The coating and substrate are exposed to the elevated temperature for a period of time in the range 10 minutes to 3 hours, preferably up to 2 hours. After this step a transparent F and Cu doped titania coating 10 has been formed on the surface.

The elevated temperature is suitably above 350° C. to ensure that crystallisation of $TiO_2$ occurs. At the same time, an upper limit of temperature is imposed by the surface being treated. Thus for example, in the case of a glass surface, a practical temperature limit of 600° C. is imposed to prevent damage to the glass.

However, it will be appreciated that in the case of certain types of glass higher temperatures may be employed, for example in the case of tempered glass, temperatures of greater than 800° C. may be employed. In the case of a glass surface, the preferred temperature range is 350-600° C. A particularly suitable temperature is 500° C. The glass substrate softens at about 450° C. and the $TiO_2$ can fuse into the surface thereof.

It will be appreciated that the period of time required to ensure adequate crystallisation of $TiO_2$ and fusing with the surface layer of the glass will vary with the temperature selected. Longer periods of time will be required at lower temperatures and shorter periods of time will be required at higher temperatures. A suitable time period when the temperature is at 500° C. is in the range of 1-2 hours. Glass will soften and will lose its morphological properties around 650° C. to 700° C. and a processing route to serve a temperature range of 400° C. to 650° C. is important. An optimum temperature range of 450° C. to 550° C. is important to attach the coatings as an immobilised part on the glass surface (by virtue of surface melting of both the titania nanomaterial and glass).

In a preferred aspect of the present teaching, annealing may be performed at 500° C. for 1 hour. The purpose of using an optimum 500° C. is to form a thin film of doped titania on the surface of glass (as indicated hereinabove, the term "thin" means approx 80 nm to 200 nm thickness for a single layer). The fusing of titania allows the glass to form an immobilised coating.

In the case of application to ceramic tiles or sanitary ware, the application temperature may be higher e.g. 700° C. as part of the second firing or 1200° C. for an unsintered tile. The temperature and time are dependent on the companies heating profile and is not standard. It is also possible and may be desirable to apply the coating at 500° C. to ceramic tiles. This is applicable to ceramic tiles, where usually there are two firings. The first firing is for sintering at around 1200 C to achieve enough density and strength (if no artwork/painting is required, this is the final sintering; however, in some cases, a second firing is required for integrating the artwork/painting on a ceramic tile. The temperature of the second firing typically ranges between 300-700 C.)

Raman Spectroscopy has been employed to confirm that whilst the anatase phase of $TiO_2$ is clearly present (approx 100%) when the heat treatment is performed at 700° C. (100%), it also remains present at higher temperatures above 1100° C. although the rutile phase dominates.

The antimicrobial solution described herein may be dried to form a powder. The resulting powder may then be added, dispersed or suspended in other sol gel or related materials and can be used as a coating formulation.

The solution may also be dried to a gel and re-dissolved or re-dispersed using an acid or solvents and applied by a variety of methods.

Alternatively, the solution may be annealed to a powder at a temperature above 350° C., but below 1350° C. for a period of time. The higher the temperature the shorter the furnace time required. As an example, at 500° C. the powder can be annealed for less than 1 hour, whereas at 1350° C. the powder can be annealed for less than 30 minutes, for example for 20 minutes.

The resulting powder may then be deposited directly on a substrate, for example by deposition or added as an additive to a coating. This coating may for example be an epoxy or silane based coating or an aqueous based coating.

Where the substrate cannot be heated at high temperature, the use of the photocatalytic solution annealed to a powder and then added in a coating (e.g. paint, sol-gel) as part of a dopant may be used.

It has been found that in order to be effective within an aqueous based solution, it may be necessary to fluorinate the solution. It is believed that this necessary to increase the concentration of $TiO_2$ nanoparticles on the surface when the coating dries. Experiments have shown that where a $TiO_2$ powder was added to a sol-gel coating, without fluorinating, minimal $TiO_2$ was detected by Raman Spectroscopy. In contrast, with fluorination, $TiO_2$ is clearly detectable by Raman spectroscopy. Suitable fluorinating agents are, for example, trifluoroacetic acid and sodium fluoride.

Although the process described herein is described with respect to the preparation of a visible light active antimicrobial coating and the deposition thereof on a glass substrate, the skilled person will appreciate that the process may be adapted for use with substrates that require high temperature processing, for example for processing at or above 1350° C.

The sol described herein is relatively stable. It has a shelf life of over one month when stored in appropriate conditions. For example, it has a shelf life of at least one week when stored at 18° C. and at least three months when stored at 5° C. Such stability is highly desirable and makes the antimicrobial coating solution suitable for industrial application.

The process according to one aspect of the present teaching enables the preparation of a transparent visible light active antimicrobial coating. The degree of transparency of the coating may be improved by varying the concentration of the components of the solution.

As discussed above, thinner coatings are desirable on glass to avoid visible effects. Accordingly, using a metal, e.g. copper, precursor can reduce the thickness of coating required whilst ensuring it remains effective thus resulting in an effective transparent coating.

Furthermore, as the coating is prepared using an excess of water, a thin layer of coating is obtained. For coatings on transparent substrates, the advantages are that there is no visible rainbow\sheen effect or powder formation present with the coating.

The antimicrobial activity of glass substrates coated with the visible light activated (doped) coating composition according to the present teaching was tested as described below in Example 2.

EXAMPLE 2

Antimicrobial testing of glass samples

Exposure time of sample was 24 hours with lighting conditions being:
1. No light
2. T5 light 1000 Lux (light box) in a moist environment (wet filter paper placed in petri dish)
    Tested organism: *Staphylococcus aureus* ATCC 6538
    Procedure followed was based on ISO 27447:2009 standard, modified for visible light activation.

Briefly, an overnight culture of *S. aureus* was washed with phosphate buffer saline (PBS) twice. For the analysis, each sample was aseptically placed in a sterile petri dish containing moist filter paper and inoculated with the bacterial suspension containing approximately $1\times10^6$ colony forming units (CFU)/sample. The prepared samples were divided into two groups (test sample (i.e. with coating) and control (no coating)). One of the control samples was tested immediately for viable bacterial count using the pour plate method in triplicate. Dilutions as far as $10^{-5}$ were made and were incubated aerobically at 37° C. overnight after which a colony count was performed. The results are presented in Table 2 below.

The remainder of the prepared samples were divided between a light proof chamber and exposure to T5 lighting (1000 lux) for 24 hours at room temperature.

Following incubation (24 hours), all samples were processed to analyse for viable bacteria remaining on the surface, post-exposure. All resulting plates were incubated aerobically at 37° C. for 24 hours (or overnight) after which a colony count was performed. The results are presented in Table 2 below.

TABLE 2

Results of microbial testing on glass samples

| dilutions | Control | Sample 1 | Sample 2 | Sample 3 |
|---|---|---|---|---|
| | | 0 h | | |
| $10^{-3}$ | TNTC | | | |
| $10^{-4}$ | *15, 12, 16 | | | |
| $10^{-5}$ | 1, 0, 0 | | | |
| $10^{-6}$ | 0 | | | |
| $10^{-7}$ | 0 | | | |
| cfu/sample | $1.4 \times 10^6$ | | | |
| | | 24 h Dark | | |
| neat | | *26, 20 | 0 | 4, 7 |
| $10^{-1}$ | | 2, 4 | 0 | 4, 3 |
| $10^{-2}$ | | 0 | 0 | 1, 0 |
| $10^{-3}$ | TNTC | 0 | 0 | 0 |
| $10^{-4}$ | *22, 18 | 0 | 0 | 0 |
| $10^{-5}$ | 4, 2 | | | |
| cfu/sample | $2.0 \times 10^6$ | $2.3 \times 10^2$ | 0 | 0** |
| | | 24 h Light | | |
| neat | | 1, 4 | 1, 1 | 0 |
| $10^{-1}$ | | 0, 2 | 0 | 0 |

TABLE 2-continued

Results of microbial testing on glass samples

| dilutions | Control | Sample 1 | Sample 2 | Sample 3 |
|---|---|---|---|---|
| $10^{-2}$ | | 0 | 0 | 0 |
| $10^{-3}$ | *18, 11 | 0 | 0 | 0 |
| $10^{-4}$ | 0 | 0 | 0 | 0 |
| $10^{-5}$ | 0 | | | |
| cfu/sample | $1.5 \times 10^5$ | 0** | 0** | 0 |

*indicates those results used for average data
**indicates a count so low as to indicate complete kill With reference to the results in Table 2, the agreement between control samples at time 0 H and time 24 H is within expectations, and no significant log reduction is evident. Each treated glass sample (samples 1 to 3) was compared to the relevant control at time 24 H in order to provide a corrected comparison control. Treated glass samples showed a reduction in bacterial numbers, under both dark and light conditions, with no significant difference between light and dark conditions.

The results demonstrated that the glass samples coated with the visible light activated (doped) coating according to the present teaching have an antimicrobial effect.

Whilst, experimental data shows that the doped VLA works on glass, the non doped pure VLA solution has also been shown to be antimicrobial in experiments on coatings annealed at high temperatures on ceramic tiles. It is to be highlighted that thicker coatings may be employed on ceramics and so the results are not necessarily comparable with the previous experiments on glass.

The tables below provide results demonstrating the antimicrobial performance of the non-doped coating.

TABLE 3

Coating Performance against MRSA under Visible light of a coated ceramic tile

| SAMPLE | Exposure | Dilution | Colony Count | CFU/ml recovery |
|---|---|---|---|---|
| A3 (1) | LIGHT | $10^{-0}$ | 0, 0 | 0 |
| | | $10^{-1}$ | 0, 0 | |
| | | $10^{-2}$ | 0, 0 | |
| A3 (2) | | $10^{-0}$ | 0, 0 | 0 |
| | | $10^{-1}$ | 0, 0 | |
| | | $10^{-2}$ | 0, 0 | |
| A3 (3) | | $10^{-0}$ | 0, 0 | 0 |
| | | $10^{-1}$ | 0, 0 | |
| | | $10^{-2}$ | 0, 0 | |
| A3 (1) | DARK | $10^{-0}$ | TNTC, TNTC | $5.3 \times 10^5$ |
| | | $10^{-1}$ | TNTC, TNTC | |
| | | $10^{-2}$ | 125, 140 | |
| A3 (2) | | $10^{-0}$ | TNTC, TNTC | $5.3 \times 10^5$ |
| | | $10^{-1}$ | TNTC, TNTC | |
| | | $10^{-2}$ | 90, 165 | |
| A3 (3) | | $10^{-0}$ | TNTC, TNTC | $5.3 \times 10^5$ |
| | | $10^{-1}$ | TNTC, TNTC | |
| | | $10^{-2}$ | 108, 89 | |

It will be appreciated from table 3 that a Log 5 reduction, i.e. 99.999% of all MRSA on the three samples was killed in the presence of visible light demonstrating the effectiveness of the coating. In contrast, when in the dark there was no noticeable antimicrobial effect.

TABLE 4

Coating Performance against a Fungi; *T. Rubum*. Coated Tile with pure VLA solution and tested against *T Rubum* under Visible light

| SAMPLE | Exposure | Dilution | Colony Count | CFU/ml recovery |
|---|---|---|---|---|
| A3 (1) | LIGHT | $10^{-0}$ | 0, 0 | 0 |
|  |  | $10^{-1}$ | 0, 0 |  |
|  |  | $10^{-2}$ | 0, 0 |  |
| A3 (2) |  | $10^{-0}$ | 43, 33 | $0.8 \times 10^4$ |
|  |  | $10^{-1}$ | 7, 0 |  |
|  |  | $10^{-2}$ | 0, 0 |  |
| A3 (3) |  | $10^{-0}$ | 1, 0 | 0 |
|  |  | $10^{-1}$ | 0, 0 |  |
|  |  | $10^{-2}$ | 0, 0 |  |
| A3 (1) | DARK | $10^{-0}$ | TNTC, TNTC | $1.3 \times 10^6$ |
|  |  | $10^{-1}$ | TNTC, TNTC |  |
|  |  | $10^{-2}$ | 68, 60 |  |
| A3 (2) |  | $10^{-0}$ | TNTC, TNTC | $1.3 \times 10^6$ |
|  |  | $10^{-1}$ | TNTC, TNTC |  |
|  |  | $10^{-2}$ | 62, 70 |  |
| A3 (3) |  | $10^{-0}$ | TNTC, TNTC | $1.1 \times 10^6$ |
|  |  | $10^{-1}$ | TNTC, TNTC |  |
|  |  | $10^{-2}$ | 54, 53 |  |

It will be appreciated from table 4 that the coating resulted in a Log 3 reduction i.e. 99.9% effective in killing *T. Rubum* on the three samples in the presence of visible light demonstrating the effectiveness of the coating. When in the dark there was no noticeable antimicrobial effect.

TABLE 5 calculation of inoculum concentration used for tiles for Tests #1 and #2

|  | Count (cfu/ml) | Dilution | Inoculum for tiles (cfu/ml) |
|---|---|---|---|
| Test #1 | | | |
| Haemocytometer | $4.7 \times 10^8$ | 1/470 | $1 \times 10^6$ |
| Plate count | $9.5 \times 10^8$ | 1/470 | $2 \times 10^6$ |
| Test #2 | | | |
| Haemocytometer | $4.5 \times 10^8$ | 1/450 | $1 \times 10^6$ |
| Plate count | $1.2 \times 10^9$ | 1/450 | $2.6 \times 10^6$ |

TABLE 6

Coating Performance against *E. Coli* when an annealed coating on a ceramic tile is tested

| SAMPLE | # | Light CFU/Plate | Light CFU/tile | Dark CFU/plate | Dark CFU/tile |
|---|---|---|---|---|---|
| Blank | 1 | TNTC* | TNTC | TNTC | TNTC |
|  | 2 | TNTC | TNTC | TNTC | TNTC |
|  | 3 | TNTC | TNTC | TNTC | TNTC |
|  | 4 | TNTC | TNTC | TNTC | TNTC |
| A1 | 1 | 0 | 0 | TNTC | TNTC |
|  | 2 | 0 | 0 | TNTC | TNTC |
|  | 3 | 0 | 0 | TNTC | TNTC |
|  | 4 | 0 | 0 | TNTC | TNTC |
|  | 5 | 0 | 0 | TNTC | TNTC |
| A2 | 1 | 0 | 0 | TNTC | TNTC |
|  | 2 | 24 | 480 | 31 | 620 |
|  | 3 | 0 | 0 | 206 | 4120 |
|  | 4 | 0 | 0 | TNTC | TNTC |
| B1 | 1 | TNTC | TNTC | 0 | 0 |
|  | 2 | 20 | 400 | TNTC | TNTC |
|  | 3 | 274 | 5480 | TNTC | TNTC |
|  | 4 | 47 | 940 | 0 | 0 |
|  | 5 | 8 | 160 | TNTC | TNTC |

Table 6 demonstrates that the blank and sample in the dark showed no antibacterial effect. The presence of visible light killed *E. Coli* on the coated tile with a log 5 reduction, i.e. 99.999% of all *E. coli* killed on coated tile on sample A1.

By varying the concentration of the coating it is possible to vary both transparency and performance. A thin coating (G2) and a thick coating (G1) were tested against E. *Coli* with the pure VLA Solution. The results are shown in Table 7.

TABLE 7

Mean recovery of *E. coli* per sample for each test condition with log reduction calculated.

| Sample | Total no. of cells inoculated onto each sample | Mean recovery post incubation | Log reduction |
|---|---|---|---|
| G1 | $1.9 \times 10^6$ | $2.1 \times 10^2$ | 4 |
| G2 | $1.9 \times 10^6$ | $6.3 \times 10^4$ | 1.5 |

The greatest reduction in microbial load (4 log) was observed from sample G1. Glass panel G2 was an identical glass panel to G1 but was treated with a very thin coating. A 1.5 log reduction in bacterial load was observed from glass panel G2.

The present application has been described generally in the context of a coating for glass. It will however be appreciated that the coating process is not limited to use with glass and may be used with other materials, including ceramics. It will be appreciated that a general limitation with respect to which materials may be coated is imposed by the melting temperature of the material, as the melting temperature should be above that used in the coating process.

Additionally, whilst the coating described herein is useful for its antimicrobial properties, it may also provide other advantages including improved scratch resistance.

In the present application references to wt % are to be taken to mean % wt/wt.

The words comprises/comprising when used in this specification are to specify the presence of stated features, integers, steps or components but does not preclude the presence or addition of one or more other features, integers, steps, components or groups thereof.

The invention claimed is:

1. A process for the preparation of an antimicrobial coating solution comprising a hydrolysed fluorine- and copper-doped titanyl acetate transparent sol, the process comprising the steps of:
   (i) mixing a chelating agent with a titanium alkoxide and fluoroacetic acid; and
   (ii) adding an aqueous solution to the mixture formed from step (i).

2. A process according to claim 1, wherein the chelating agent is a carboxylic acid.

3. A process according to claim 2, wherein the carboxylic acid is selected from the group consisting of formic acid, propionic acid, butanoic acid and acetic acid.

4. A process according to claim 2, wherein the carboxylic acid is acetic acid and wherein the acetic acid is in the form of glacial acetic acid.

5. A process according to claim 4, wherein the amount of glacial acetic acid used is in the range 1 to 20 wt %.

6. A process according to claim 4, wherein the amount of glacial acetic acid used is in the range 2 to 10 wt %.

7. A process according to claim 4, wherein the amount of glacial acetic acid used is in the range 1 to 40 wt %.

8. A process according to claim 1, wherein the titanium alkoxide is selected from the group consisting of titanium isopropoxide, titanium ethoxide, titanium methoxide and titanium butoxide.

9. A process according to claim 8, wherein the titanium alkoxide is titanium isopropoxide.

10. A process according to claim 8, wherein the titanium alkoxide is titanium isopropoxide and wherein the amount of titanium isopropoxide used is in the range 4 to 15wt %.

11. A process according to claim 8, wherein the titanium alkoxide is titanium isopropoxide and wherein the amount of titanium isopropoxide used is in the range 6 to 12 wt %.

12. A process according to claim 1, wherein the fluoroacetic acid is one of mono fluoroacetic acid, difluoroacetic acid or trifluoroacetic acid.

13. A process according to claim 12, wherein the amount of trifluoroacetic acid used is in the range 0.1 to 20 wt %.

14. A process according to claim 12, wherein the amount of trifluoroacetic acid used is in the range 0.1 to 10 wt %.

15. A process according to claim 12, wherein the amount of trifluoroacetic acid used is in the range 2 to 8 wt %.

16. A process according to claim 1 comprising the step of adding a metal precursor.

17. A process according to claim 16, wherein the metal precursor comprises one of copper, silver, and zinc.

18. A process according to claim 17, wherein the metal precursor comprises a sulphate or nitrate of the metal.

19. A process according to claim 17, wherein the metal precursor is copper (II) nitrate pentahemihydrate.

20. A process according to claim 19, wherein the amount of copper (II) nitrate pentahemihydrate used is in the range 0.03 to 3 wt %.

21. A process according to claim 19, wherein the copper (II) nitrate pentahemihydrate is dissolved within the aqueous solution prior to the step of adding to the mixture from step (i).

22. A process according to claim 1, wherein the amount of water in the solution is at least 30% by wt.

23. A process according to claim 22, wherein the amount of water used is in the range 30 to 99.5 wt %.

24. A process according to claim 1, wherein the fluoroacetic acid is trifluoroacetic acid.

25. A process for making an antimicrobial powder comprising the initial step of preparing a solution in accordance with claim 1 and then annealing the solution at a temperature between 350° C. and 1350° C.

26. A method of preparing an antimicrobial coating comprising the step of mixing an antimicrobial powder as prepared by the process of claim 25 with a coating composition and wherein the coating composition is an aqueous solution and the method comprises the step of fluorinating the solution with a fluorinating agent.

27. An antimicrobial coating composition obtained by the process according to claim 1, wherein the coating composition is visible light activated.

28. An antimicrobial coating composition according to claim 27, which is stable at temperatures up to 1350° C.

29. An antimicrobial coating composition comprising a hydrolysed fluorine- and copper-doped titanyl acetate transparent sol.

30. A process for the preparation of an antimicrobial coating solution, the process comprising the steps of:
(i) mixing a chelating agent with a titanium alkoxide and fluoroacetic acid; and
(ii) adding an aqueous solution to the mixture formed from step (i) wherein the amount of water in the solution is at least 30% by wt.

* * * * *